(12) United States Patent
Aduri et al.

(10) Patent No.: US 9,624,248 B2
(45) Date of Patent: Apr. 18, 2017

(54) IONIC LIQUID COMPOUND

(71) Applicant: RELIANCE INDUSTRIES LIMITED, Mumbai, Maharashtra (IN)

(72) Inventors: Pavankumar Aduri, Maharashtra (IN); Parasu Veera Uppara, Maharashtra (IN); Viswanath Kotra, Andhra Pradesh (IN); Mangesh Sakhalkar, Maharashtra (IN); Vibhuti Dukhande, Maharashtra (IN)

(73) Assignee: Reliance Industries Limited, Mumbai, Maharashtra (IN)

( * ) Notice: Subject to any disclaimer, the term of this patent is extended or adjusted under 35 U.S.C. 154(b) by 0 days.

(21) Appl. No.: 14/784,742

(22) PCT Filed: Apr. 21, 2014

(86) PCT No.: PCT/IN2014/000254
§ 371 (c)(1),
(2) Date: Oct. 15, 2015

(87) PCT Pub. No.: WO2014/178075
PCT Pub. Date: Nov. 6, 2014

(65) Prior Publication Data
US 2016/0060277 A1    Mar. 3, 2016

(30) Foreign Application Priority Data

Apr. 19, 2013    (IN) .......... 1456/MUM/2013

(51) Int. Cl.
| | |
|---|---|
| *C07F 5/06* | (2006.01) |
| *C07F 9/90* | (2006.01) |
| *B01J 37/04* | (2006.01) |
| *C07C 37/16* | (2006.01) |
| *C07C 2/26* | (2006.01) |
| *C07C 45/45* | (2006.01) |
| *C01F 7/00* | (2006.01) |
| *C07C 2/66* | (2006.01) |
| *C07C 2/86* | (2006.01) |
| *C07C 67/293* | (2006.01) |
| *C07C 211/63* | (2006.01) |
| *C07C 45/46* | (2006.01) |
| *B01J 31/02* | (2006.01) |
| *C07C 2/68* | (2006.01) |

(52) U.S. Cl.
CPC .......... *C07F 5/069* (2013.01); *B01J 31/0298* (2013.01); *B01J 37/04* (2013.01); *C01F 7/00* (2013.01); *C07C 2/26* (2013.01); *C07C 2/66* (2013.01); *C07C 2/68* (2013.01); *C07C 2/861* (2013.01); *C07C 37/16* (2013.01); *C07C 45/45* (2013.01); *C07C 45/46* (2013.01); *C07C 67/293* (2013.01); *C07C 211/63* (2013.01); *C07F 9/904* (2013.01); *C07C 2101/16* (2013.01); *C07C 2527/125* (2013.01); *C07C 2531/02* (2013.01)

(58) Field of Classification Search
CPC ... C07F 7/00; C07F 5/069; C07F 9/904; B01J 31/0298; B01J 37/04; C07C 2/26; C07C 2/66; C07C 2/68; C07C 2/861; C07C 37/16; C07C 45/45; C07C 45/46; C07C 67/293; C07C 211/63
USPC ....... 556/28, 30, 64, 176; 560/231; 568/312, 568/716; 585/454, 456, 504, 521
See application file for complete search history.

(56) References Cited

U.S. PATENT DOCUMENTS

| | | |
|---|---|---|
| 3,104,267 A | 9/1963 | Antonsen et al. |
| 3,249,650 A | 5/1966 | Fenske |
| 3,346,657 A | 10/1967 | Henke et al. |
| 3,494,971 A | 2/1970 | Fenske |
| 3,560,587 A | 2/1971 | Borst, Jr. |
| 3,686,354 A | 8/1972 | Hervert |
| 3,713,615 A | 1/1973 | Jones |
| 3,950,448 A | 4/1976 | Witt |

(Continued)

FOREIGN PATENT DOCUMENTS

| | | |
|---|---|---|
| WO | 98/03454 A1 | 1/1998 |
| WO | 99/03163 A1 | 1/1999 |
| WO | 00/41809 A1 | 7/2000 |

OTHER PUBLICATIONS

International Search Report of PCT/IN2014/000254, mailed Oct. 30, 2014.

(Continued)

*Primary Examiner* — Porfirio Nazario Gonzalez
(74) *Attorney, Agent, or Firm* — Collard & Roe, P.C.

(57) ABSTRACT

The present disclosure provides an ionic liquid compound of Formula (I) and its application in reactions such as alkylation, arylation, acylation, diels alder and oligomerization, Formula I $[(NR_1R_2R_3)_iM_1]^{n+}[(M_2Y_k)_LX_j]^{n-}$ The present disclosure also provides a process for preparing the ionic liquid compound of Formula (I) which involves preparing an ionic salt complex represented by Formula $[(NR_1R_2R_3)_iM_1]^{n+}[X_j]^{n-}$ by mixing an amine represented by Formula $NR_1R_2R_3$ and a metal salt represented by formula $M_1X_j$; and mixing the ionic salt complex and a metal salt represented by formula $M_2Y_k$ to obtain the ionic liquid compound.

20 Claims, 3 Drawing Sheets

(56) References Cited

U.S. PATENT DOCUMENTS

Figure 1:
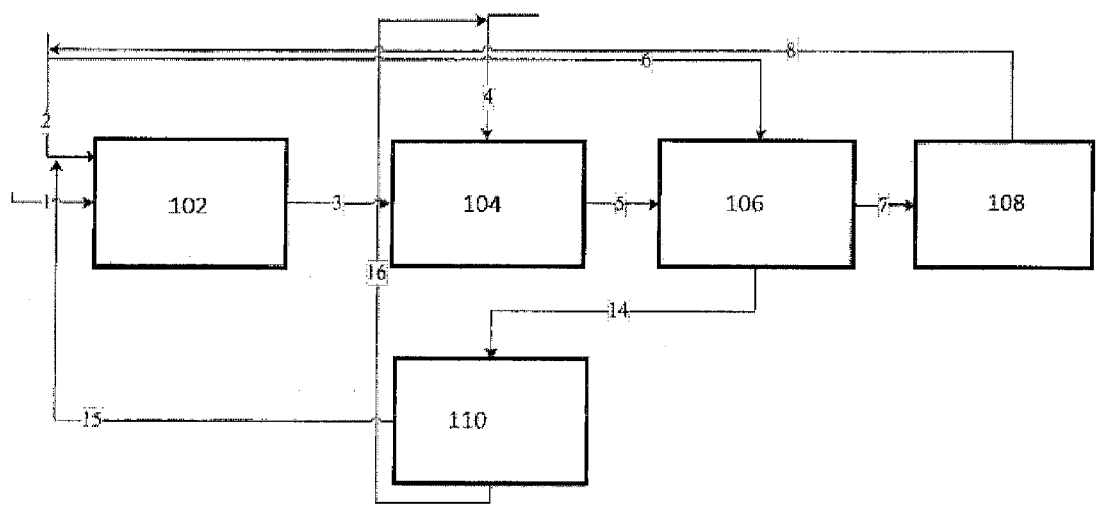

| | | |
|---|---|---|
| 4,219,686 A | 8/1980 | Petrillo et al. |
| 4,239,931 A | 12/1980 | Mikulicz |
| 4,358,628 A | 11/1982 | Slaugh |
| 4,368,342 A | 1/1983 | Slaugh |
| 4,513,156 A | 4/1985 | Tabak |
| 4,973,780 A | 11/1990 | Johnson et al. |
| 5,196,574 A | 3/1993 | Kocal |
| 5,196,624 A | 3/1993 | Threlkel et al. |
| 5,284,993 A | 2/1994 | Eastman |
| 5,334,793 A | 8/1994 | Kocal |
| 5,344,997 A | 9/1994 | Kocal |
| 5,574,198 A | 11/1996 | Radici et al. |
| 5,777,187 A | 7/1998 | Knifton et al. |
| 5,824,832 A | 10/1998 | Sherif et al. |
| 5,847,254 A | 12/1998 | Knifton et al. |
| 5,894,076 A | 4/1999 | Hearn et al. |
| 6,133,492 A | 10/2000 | Anantaneni |
| 7,285,698 B2 | 10/2007 | Liu et al. |
| 7,655,824 B2 | 2/2010 | Riley et al. |
| 7,737,312 B2 | 6/2010 | Greager et al. |
| 2010/0094072 A1 | 4/2010 | Randolph et al. |
| 2011/0118517 A1 | 5/2011 | Sohn et al. |
| 2011/0144403 A1 | 6/2011 | Jan et al. |
| 2012/0169298 A1* | 7/2012 | Martin ............ H01G 11/58 320/166 |

OTHER PUBLICATIONS

Dupont et al,. Ionic Liquid (Molten Salt) Phase Organometallic Catalysis, Chem. Rev. 2002,102, 3667-3692.

Wasserscheid et al., Ionic Liquids-New "Solutions" for Transition Metal Catalyss, Agnew. Chem. Int. Ed. 2000, 39, 3772-3789.

* cited by examiner

IONIC LIQUID COMPOUND

CROSS REFERENCE TO RELATED APPLICATIONS

This application is the National Stage of PCT/IN2014/000254 filed on Apr. 21, 2014, which claims priority under 35 U.S.C. §119 of Indian Application No. 1456/MUM/2013 filed on Apr. 19, 2013, the disclosures of which are incorporated by reference.

FIELD

The present disclosure relates to an ionic liquid compound and its preparation. The present disclosure also relates to the use of ionic liquid compound for catalysing the chemical reactions.

BACKGROUND

Ionic liquids are liquids that are composed entirely of ions or a combination of cations and anions. The "low temperature" ionic liquids are generally organic salts with melting points less than 100 degrees C., often even lower than room temperature. Ionic liquids may be suitable, for example, for use as catalysts and solvents in alkylation and polymerization reactions as well as in dimerization, oligomerization acetylation, metatheses and copolymerization reactions.

One class of ionic liquids is fused salt compositions, which are molten at low temperature and are useful as catalysts, solvents and electrolytes. Such compositions are mixtures of components which are liquids at temperatures below the individual melting points of the components.

Ionic liquids can be defined as liquids whose make-up entirely comprises ions as a combination of cations and anions. The most common ionic liquids are those prepared from organic-based cations and inorganic or organic anions. The most common organic cations are ammonium cations, however phosphonium and sulphonium cations are also frequently used. Ionic liquids of pyridinium and imidazolium are perhaps the most commonly used cations. Anions include, but are not limited to BF4-, PF6-, haloaluminates such as $Al_2Cl_7$- and $Al_2Br_7$-, [$(CF_3SO_2)_2N$)]—, alkyl sulphates ($RSO_3$—), carboxylates ($RCO_2$—) and the like. The most catalytically interesting ionic liquids are those derived from ammonium halides and Lewis acids (such as $AlCl_3$, $TiCl_4$, $SnCl_4$, $FeCl_3$ and the like). Chloroaluminate ionic liquids are perhaps the most commonly used ionic liquid catalyst systems.

The alkylation of benzene with acyclic olefins is a widely practiced commercial process. This process is performed to produce a variety of chemical compounds which may be end products or may be used as intermediates in the production of other valuable industrial chemicals. One of the most significant processes for the alkylation of aromatic hydrocarbons employs liquid phase HF as a catalyst and is performed to produce alkyl benzenes which are further converted into detergents by sulfonation and neutralization.

U.S. Pat. No. 3,249,650 discloses the use of an HF catalyst for the reaction of isoparaffin and olefin. The reaction involves passing the iosparaffin-olefin stream in to an alkylation reactor along with an HF catalyst and continuously withdrawing a portion of hydrocarbon-HF mixture.

U.S. Pat. No. 3,494,971 discloses alkylation of benzene with $C_{10}$-$C_{15}$ olefins in two stages with hydrogen fluoride as a catalyst at 100° F. temperature. The HF catalyst employed in the first stage is a used catalyst and the HF used in the second stage is a fresh or regenerated catalyst.

U.S. Pat. No. 3,560,587 discloses the use of hydrogen fluoride catalyst for the alkylation of isoparaffin with olefin. In the process, a mixture is passed into a reaction cooler equipped with an internally placed heat exchanger, wherein the mixture is contacted with HF catalyst under isothermal reaction conditions and the reaction effluent is then passed into a reaction soaker equipped with a number of spaced perforated plates therein in which further alkylation takes place.

U.S. Pat. No. 3,686,354 discloses a method of producing high octane paraffinic motor fuel by alkylating isobutene and a C4 mono olefin in the presence of hydrogen fluoride catalyst. U.S. Pat. No. 3,713,615 discloses an alkylation fractionator having a settling section for separating liquid catalyst from the effluent of an alkylator. The lighter isoparaffins are stripped off from the heavier fractions in a fractionation section below the acid settling section.

U.S. Pat. No. 4,239,931 discloses hydrofluoric acid-catalyzed alkylation of an isobutane with a mixture of propylene and butylene at 200° F. in an isoparaffin stripping column-integrated acid catalyst regeneration system.

U.S. Pat. No. 3,950,448 discloses production of detergent grade alkylate by HF acid catalysed reaction of aromatic hydrocarbons and an olefinic hydrocarbon. The process describes the use of unique fractionation facility for the recovery and use of an aromatic concentrate and recovery of detergent alkylate product.

Use of Lewis acid catalysts has also been disclosed for alkylation. U.S. Pat. No. 3,104,267 discloses a method of preparing alkyl aromatic hydrocarbons by contacting ethylene with benzene, toluene & xylene containing catalytic mixture of titanium tetrachloride and alkyl aluminium dichloride/dialkyl aluminium chloride/alkylaluminium sesquichloride, where the ethylene is polymerized to a long chain olefin without substantial reaction of said aromatic and then contacting the reaction mixture with dry HCl/HBr, whereby the said long chain olefin alkylates to aromatic hydrocarbon. The temperature range used was 100-400° F.

U.S. Pat. No. 4,219,686 discloses a method of producing heavy alkyl benzenes and linear dodecyl benzene comprising of two steps. Auto-condensation of $C_{11}$ to $C_{14}$ olefins in the presence of Aluminum chloride catalyst followed by alkylation of benzene with the above reaction mixture in the presence of aluminum Chloride where the mixture is saturated with gaseous hydrogen chloride at 40-42° C.

U.S. Pat. No. 5,284,993 discloses a method of regeneration of catalyst used for alkylation of olefins by isoparaffins. The catalyst comprises of fluorosulphonic acid/triflouoromethanesulphonic acid and methanesulphonic acid. The process mainly describes the removal of acid soluble oils (ASO) produced as an undesirable by-product during the reaction. The process includes the use of water to induce the formation of the two immiscible phases of ASO and methanesulphonic acid.

US20100094072A1 discloses the use of a catalyst for the isoparaffin-olefin alkylation. The catalyst is obtained by admixing a trifluoromethanesulfonic acid on a polyacrylic acid support. It was also found that the use of solid catalysts facilitates the production of linear alkyl benzenes. U.S. Pat. No. 5,334,793 discloses the use of HF solid acid catalyst for the alkylation of benzene with olefin feed stock obtained from dehydrogenation unit containing linear paraffin having 8 to 16 carbon atoms.

U.S. Pat. No. 7,737,312 discloses the use of UOP DETAL solid acid catalyst for the production of linear alkyl benzene (LAB) from the olefin stream obtained from Fischer-Tropsch reaction. The above obtained stream is reacted with benzene to produce LAB.

Similarly, several other solid catalysts were reported so far for the alkylation reaction: U.S. Pat. Nos. 3,346,657, 4,358,628, 4,368,342, 4,513,156, 4,973,780, 5,196,574, 5,196,624, 5,344,997, 5,574,198, 5,777,187, 5,847,254, 5,894,076, 6,133,492, 7,655,824, US2011/0118517, US20110144403.

Further, several ionic liquid catalysts were reported for alkylation reaction. For instance, WO/1998/003454 discloses the use of alkyl-containing amine hydrohalide ionic liquids for the reaction of benzene with an olefin having an average carbon content of over 10, a chloroalkane having an average carbon content of over 6, or mixture thereof.

U.S. Pat. No. 5,824,832 discloses ionic liquids comprising a mixture of a metal halide and an alkyl-containing amine hydrohalide salt for the production of linear alkyl benzene. The metal halide is a covalantly bonded metal halide which can contain a metal selected from the group comprised of aluminum, gallium, iron, copper, zinc and indium.

WO/1999/003163 discloses alkylation of aromatic compounds using a catalyst which comprises a porous support impregnated with an ionic liquid consisting of an organic base and a metal. Organic base is selected from the group consisting of a halide of imidazolium, pyridinium, sulfonium, phosphonium, guanidinium, and ammonium and metal halide is selected from the group comprised of aluminum, gallium, iron, copper, zinc, and indium.

WO/2000/041809 discloses the use of catalyst comprising a pre-formed complex of an ionic liquid and an aromatic hydrocarbon for the alkylation of aromatic hydrocarbons with $C_2$ to $C_{10}$ olefin. The ionic liquid comprises a first component of the formula $R_nMX3_{-n}$ (wherein R is a $C_1$-$C_5$ alkyl group, M is aluminium or gallium, X is a halogen atom) and a second component selected from the group consisting of an alkyl ammonium halide, an imidazolium halide, a pyridinium halide, a hydrocarbyl substituted quaternary ammonium halide, a hydrocarbyl substituted quaternary phosphonium halide and mixtures thereof.

U.S. Pat. No. 7,285,698 discloses a method for alkylation of isobutane and $C_4$ olefin using a composite ionic liquid as a catalyst. The ionic liquid comprises a cation which is a hydrohalide of an alkyl-containing amine or pyridine and an anion which is a mixture of aluminum halide and halides or sulphates or nitates of copper, iron, zinc, nickel, cobalt, molybdenum or platinum.

The ionic liquid catalysts as disclosed in the prior art documents are found to be less effective when used in the alkylation reactions. Further, these known ionic liquid catalysts are expensive. Accordingly, there is felt a need for a cost-effective ionic liquid compound which can effectively catalyze Friedel crafts reactions such as alkylation reactions.

OBJECTS

Some of the objects of the present disclosure, which at least one embodiment herein satisfies, are as follows:

It is an object of the present disclosure to provide an ionic salt complex as a precursor of ionic liquid compound.

It is another object of the present disclosure to provide a simple and cost effective process for the preparation of ionic salt complex.

It is still another object of the present disclosure to provide a process for the preparation of ionic salt complex in the presence or absence of a solvent.

It is another object of the present disclosure to provide a cost-effective ionic liquid compound which can be used as a catalyst and/or solvent.

It is still another object of the present disclosure to provide a simple and cost effective process for the preparation of an ionic liquid compound.

It is yet another object of the present disclosure to provide a process for the preparation of an ionic liquid which can be carried out in the presence of a solvent to achieve the desired viscosity of the ionic liquid.

It is a further object of the present disclosure to provide an ionic liquid catalyst which can be used for Diels-Alder reaction, Friedel crafts reactions such as alkylation, acylation, alkyl-sulfonation, and the like.

It is still further object of the present disclosure to provide a recycled ionic liquid compound which can be used as a catalyst in an alkylation reaction.

It is another object of the present disclosure to provide an ionic liquid catalysed Diels-Alder reaction, Friedel crafts reactions such as alkylation, acylation, alkyl-sulfonation, and the like.

It is another object of the present disclosure to provide a simple and cost effective alkylation reaction using the ionic liquid compound.

It is another object of the present disclosure to an alkylation reaction in which the used ionic liquid catalyst can be easily recovered and recycled.

SUMMARY

The present disclosure provides an ionic liquid compound of Formula (I);

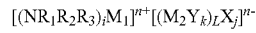

Formula I wherein,
NR$_1$R$_2$R$_3$ represents an amine,
R$_1$, R$_2$ and R$_3$ are independently selected from the group consisting of alkyl, aryl and H,
M$_1$ or M$_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof,
X or Y is selected from the group consisting of halogen, nitrate, sulphate, sulfonate, carbonate, phosphonate and acetate,
'n' represents 1 to 4,
'i' represents 1 to 6,
'j' represents 1 to 4,
'k' represents 1 to 4,
'L' represents 1 to 7,
M$_1$=M$_2$ or M$_1$≠M$_2$, and
X=Y or X≠Y.

Typically, the alkyl group is selected from the group consisting of methyl, ethyl, propyl, butyl and combinations thereof; the aryl group is selected from the group consisting of benzyl, phenyl, substituted benzenes and combinations thereof; and the halogen is selected from the group consisting of F, Cl, Br and I.

Typically, NR$_1$R$_2$R$_3$ is a trialkylamine; M$_1$ or M$_2$ is a metal selected from the group consisting of Al, Fe, Zn, Mn, Mg, Ti, Sn, Pd, Pt, Rh, Cu, Cr, Co, Ce, Ni, Ga, In, Sb, Zr and combinations thereof; and X or Y is a halogen.

In accordance with another aspect of the present disclosure there is provided a process for the preparation of an ionic liquid compound of Formula (I),

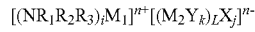

Formula I wherein,
NR$_1$R$_2$R$_3$ represents an amine,
R$_1$, R$_2$ and R$_3$ are independently selected from the group consisting of alkyl, aryl and H,
M$_1$ or M$_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof,
X or Y is selected from the group consisting of halogen, nitrate, sulphate, sulfonate, carbonate, phosphonate and acetate, 'n' represents 1 to 4,
'i' represents 1 to 6,
'j' represents 1 to 4,
'k' represents 1 to 4,
'L' represents 1 to 7,
M$_1$=M$_2$ or M$_1$≠M$_2$, and
X=Y or X≠Y,
said process comprising the following steps:
i. preparing an ionic salt complex precursor represented by Formula [(NR$_1$R$_2$R$_3$)$_i$M$_1$]$^{n+}$[X$_j$]$^{n-}$ by mixing an amine represented by Formula NR$_1$R$_2$R$_3$ and a metal salt represented by formula M$_1$X$_j$; and
ii. mixing the ionic salt complex precursor and a metal salt represented by formula M$_2$Y$_1$, to obtain the ionic liquid compound.

Typically, the step (i) is carried out at a temperature ranging from −20 to 100° C.

Typically, the step (i) is carried out in the presence of a solvent selected from the group consisting of ethyl acetate, ethanol, methanol, methyl iso butyl ketone, methyl ethyl ketone, benzene, toluene, dichloromethane and combinations thereof.

Typically, the step (ii) is carried out at a temperature ranging from −20 to 100° C.

Typically, the step (ii) is carried out in the presence of a solvent selected from the group consisting of methyl iso butyl ketone, methyl ethyl ketone, benzene, toluene, dichloromethane and combinations thereof.

Typically, the mole ratio of the amine to the metal salt ranges from 1:0.1 to 1:0.5. Typically, the mole ratio of the ionic salt complex precursor to the metal salt ranges from 1:3 to 1:6.

Typically, ionic liquid compound is [(Et$_3$N)$_3$—Al]$^{3+}$ [(AlCl$_3$)$_6$Cl$_3$]$^{3-}$ prepared by mixing triethylamine and AlCl$_3$ to form ionic salt complex precursor, [(Et$_3$N)$_3$—Al]$^{3+}$ [(Cl)$_3$]$^{3-}$; and complexing said ionic salt complex precursor with AlCl$_3$.

In accordance with still another aspect of the present disclosure there is provided an ionic salt complex precursor represented by Formula (II)

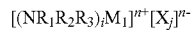

Formula II wherein,
NR$_1$R$_2$R$_3$ represents an amine,
R$_1$, R$_2$ and R$_3$ are independently selected from the group consisting of alkyl, aryl and H, M$_1$ or M$_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof,
X or Y is selected from the group consisting of halogen, nitrate, sulphate, sulfonate, carbonate, phosphonate and acetate,
'n' represents 1 to 4,
'i' represents 1 to 6, and
'j' represents 1 to 4, In accordance with yet another aspect of the present disclosure there is provided a process for preparing an ionic salt complex precursor represented by Formula [(NR$_1$R$_2$R$_3$)$_i$M$_1$]$^{n+}$[X$_j$]$^{n-}$ comprises mixing an amine represented by Formula NR$_1$R$_2$R$_3$ and a metal salt represented by formula M$_1$X$_j$.

Typically, the ionic salt complex precursor is [(Et$_3$N)$_3$—Al]$^{3+}$[(Cl)$_3$]$^{3-}$ prepared by mixing triethylamine and AlCl$_3$.

In accordance with a further aspect of the present disclosure there is provided a process for conducting at least one reaction selected from the group consisting of alkylation reaction, arylation reaction, acylation reaction, diels alder reaction and oligomerization reaction of at least one compound selected from the group consisting of C$_1$ to C$_{20}$ aliphatic compounds, C$_6$ to C$_8$ aromatic compounds and heteroaryl compounds in the presence of an ionic liquid compound represented by formula [(NR$_1$R$_2$R$_3$)$_i$M$_1$]$^{n+}$ [(M$_2$Y$_k$)$_L$ X$_j$]$^{n-}$ and at a temperature of 20 to 100° C.,
wherein,
NR$_1$R$_2$R$_3$ represents an amine,
R$_1$, R$_2$ and R$_3$ are independently selected from the group consisting of alkyl, aryl and H,
M$_1$ or M$_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof,
X or Y is selected from the group consisting of halogen, nitrate, sulphate, sulfonate, carbonate, phosphonate and acetate,
'n' represents 1 to 4,
'i' represents 1 to 6,
'j' represents 1 to 4,
'k' represents 1 to 4,
'L' represents 1 to 7,
M$_1$=M$_2$ or M$_1$≠M$_2$, and
X=Y or X≠Y.

Typically, said reaction is carried out using at least one reactant selected from the group consisting of olefins, paraffins, alkyl or aryl halides, dialkyl or diaryl sulfates, dialkyl or diaryl carbonates, alcohols, carboxylic acids, esters, thiols and carbenes.

Typically, the reactant is olefin or a mixture of olefins having carbon atoms ranging from 2 to 50.

Typically, the volume ratio of ionic liquid compound to the compound ranges from 0.01 to 1.5.

The process also includes a step of recovering and recycling of said ionic liquid compound.

Typically, said ionic liquid compound is selected from the group consisting of fresh ionic liquid compound, recycled ionic liquid compound and a combination thereof.

In one embodiment said reaction is an alkylation of benzene; said reaction comprises alkylating benzene at a temperature of 20 to 100° C., preferably at 30 to 60° C. in the presence of an ionic liquid compound represented by formula

[(NR$_1$R$_2$R$_3$)$_i$M$_1$]$^{n+}$[(M$_2$Y$_k$)$_L$ X$_j$]$^{n-}$ and at least one alkylating agent to obtain linear alkyl benzene.

Typically, the alkylating agent is a mixture of at least one $C_2$ to $C_{50}$ containing olefin and at least one $C_2$ to $C_{50}$ containing paraffin.

Typically, the alkylating agent is olefin selected from the group consisting of $C_{10}$ to $C_{14}$ olefins and mixtures thereof.

Typically, the ratio of benzene to the alkylating agent ranges from 1:1 to 20:1, preferably, 6:1 to 10:1.

Typically, the alkylation of benzene is carried out at a pressure ranging from 1 to 10 atmospheres, preferably 1 to 6 atmospheres.

BRIEF DESCRIPTION OF THE ACCOMPANYING DRAWINGS

Figure 2:
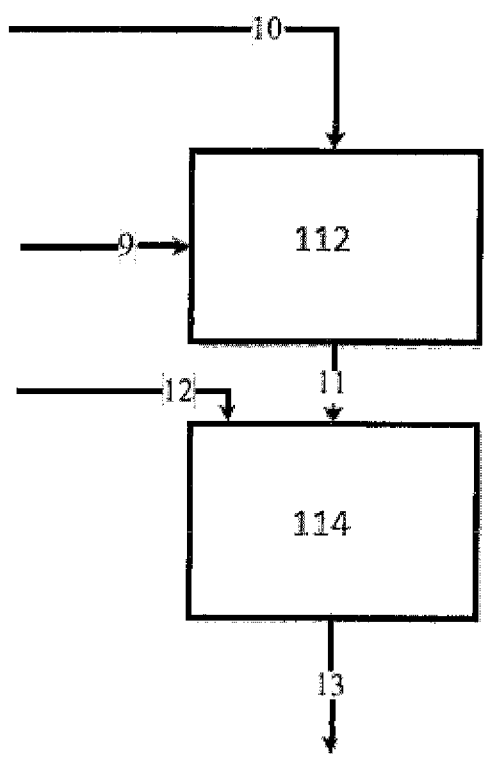
Figure 3:
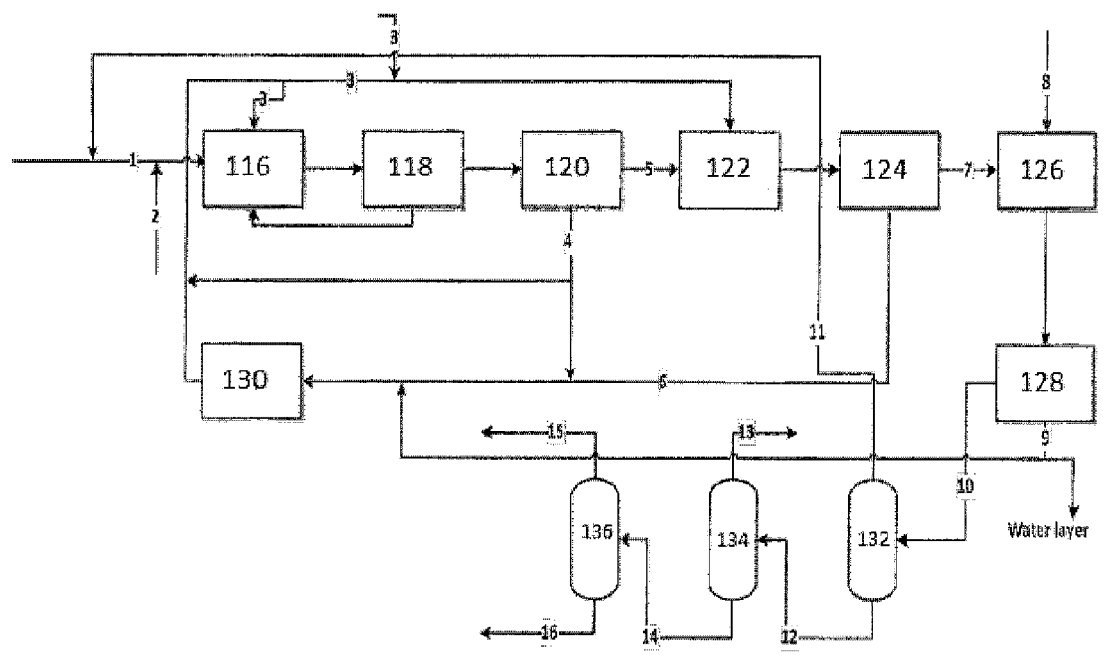

FIG. 1 illustrates a process flow diagram for the preparation of the ionic salt complex precursor;

FIG. 2 of the accompanying drawings illustrates a process flow diagram for the preparation of the ionic liquid compound; and FIG. 3 illustrates alkylation process using the ionic liquid compound of the present disclosure.

DETAILED DESCRIPTION

The present disclosure provides an ionic liquid compound which can be effectively used as a catalyst and/or solvent to catalyse the Diels-Alder reaction, Friedel crafts reactions such as alkylation, acylation, alkyl-sulfonation and the like. The ionic liquid compound of the present disclosure is represented by Formula (I)

Formula I

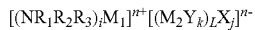
$[(NR_1R_2R_3)_iM_1]^{n+}[(M_2Y_k)_LX_j]^{n-}$

In accordance with the present disclosure, $NR_1R_2R_3$ represents an amine in which $R_1$, $R_2$ and $R_3$ are either alkyl group or aryl group or H. i.e. amine is either alkyl amine or aryl amine. The alkyl group includes but is not limited to methyl, ethyl, propyl, butyl and combinations thereof. The aryl group is selected from the group consisting of benzyl, phenyl, substituted benzenes and combinations thereof.

$M_1$ or $M_2$ is a metal selected from the group consisting of Al, Fe, Zn, Mn, Mg, Ti, Sn, Pd, Pt, Rh, Cu, Cr, Co, Ce, Ni, Ga, In, Sb, Zr and combinations thereof.

In accordance with the present disclosure, X or Y is selected from the group consisting of halogen, nitrate, sulphate, sulfonate, carbonate, phosphonate and acetate.

In accordance with the present disclosure the halogen is selected from the group consisting of F, Cl, Br and I.

In the formula I,
'n' represents 1 to 4,
'i' represents 1 to 6,
'j' represents 1 to 4,
'k' represents 1 to 4,
'L' represents 1 to 7,
$M_1=M_2$ or $M_1 \neq M_2$, and
X=Y or X≠Y.

In one embodiment $NR_1R_2R_3$ is a trialkylamine, $M_1$ or $M_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof and X or Y is a halogen.

In one exemplary embodiment the ionic liquid compound is $[(Et_3N)_3-Al]^{3+}[(AlCl_3)_6Cl_3]^{3-}$.

In accordance with another aspect of the present disclosure there is provided a process for the preparation of an ionic liquid compound of Formula (I),

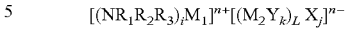
$[(NR_1R_2R_3)_iM_1]^{n+}[(M_2Y_k)_LX_j]^{n-}$

The process involves the following steps:

In the first step an ionic salt complex, represented by Formula $[(NR_1R_2R_3)_iM_1]^{n+}[X_j]^{n-}$, is prepared by mixing an amine, represented by Formula $NR_1R_2R_3$ and a metal salt represented by formula $M_1X_j$.

This first step is carried out at a temperature ranging from −20 to 100° C. and in the absence or presence a solvent. The solvent includes but is not limited to ethyl acetate, ethanol, methanol, methyl iso butyl ketone, methyl ethyl ketone, benzene, toluene, dichloromethane and combinations thereof.

In accordance with the present disclosure the mole ratio of the amine to the metal salt is maintained in the range from 1:0.1 to 1:0.5.

In the second step, the ionic salt complex and a metal salt represented by formula $M_2Y_k$ are mixed to obtain the ionic liquid compound. The mole ratio of the ionic salt complex to the metal salt is maintained in the range from 1:3 to 1:6. The second step is carried out at a temperature ranging from −20 to 100° C. in the absence or presence of a solvent. The solvent includes but is not limited to ethyl acetate, ethanol, methanol, methyl iso butyl ketone, methyl ethyl ketone, benzene, toluene, dichloromethane and combinations thereof.

The complex (ionic liquid compound) formed by reacting ionic salt complex and a metal salt is either eutectic or non-eutectic, In one exemplary embodiment the ionic liquid compound is $[(Et_3N)_3-Al]^{3+}[(AlCl_3)_6Cl_3]^{3-}$ which is prepared by mixing triethylamine and $AlCl_3$ to form an ionic salt complex precursor, $[(Et_3N)_3-Al]^{3+}[(Cl)_3]^{3-}$; and complexing the ionic salt complex precursor with $AlCl_3$.

The present disclosure also provides an ionic salt complex precursor represented by Formula (II)

Formula II

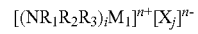
$[(NR_1R_2R_3)_iM_1]^{n+}[X_j]^{n-}$ wherein,
$NR_1R_2R_3$ represents an amine,
$R_1$, $R_2$ and $R_3$ are alkyl group or aryl group or H
$M_1$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof,
X is a halogen or a nitrate or a sulphate or sulfonate or carbonate or phosphonate or acetate,
'n' represents 1 to 4,
'i' represents 1 to 6, and
'j' represents 1 to 4, The ionic salt complex precursor represented by Formula $[(NR_1R_2R_3); M_1]^{n+}[X_j]^{n-}$ is prepared by mixing an amine represented by Formula $NR_1R_2R_3$ and a metal salt represented by formula $M_1X_j$. In one exemplary embodiment the ionic salt complex precursor is $[(Et_3N)_3-Al]^{3+}[(Cl)_3]^{3-}$ which is prepared by mixing triethylamine and $AlCl_3$.

In one embodiment of the present disclosure, $AlCl_3$ used is in a hydrated form. The present disclosure is further illustrated with the help of accompanying drawings. A process flow diagram for the preparation of the ionic salt complex precursor is illustrated in FIG. 1. The process is carried out in either batch or semi-continuous or continuous mode.

In FIG. 1 of the accompanying drawings, (102) represents a pre-mixer; the pre-mixer can be either a batch or continuous, jacketed stirred vessel or static mixer or jet mixer or pump mixer;

(104) represents a reactor where ionic salt precursor formation takes place between amine and metal halide, the reactor (104) can be a jacketed stirred vessel, static mixer, slurry reactor or combinations thereof;

(106) represents a filter where the slurry obtained from (104) is filtered. The filter (106) can be a nutsche filter or pressure nutsche filter or centrifuge or vacuum filter or agitated nutsche filter or agitated nutsche filter and dryer;

(108) represents a dryer where the precursor is dried completely to remove the residual solvent, the dryer (108) can be a tray dryer, column dryer, vacuum drier, agitated thin film dryer or a combination of a filter and a dryer such as an agitated nutsche filter and dryer;

(110) represents distillation system for the recovery of amine and solvent from the filtrate obtained from the filter (106). The distillation system (110) can be a tray or bubble or packed bed distillation column where the recovery of amine and solvent is done separately as overhead and bottom products, alternatively the (110) can also be a falling film evaporator or an agitated thin film evaporator or combination of a falling film evaporator and an agitated thin film evaporator or single or multi effect evaporator where amine and solvent are recovered as a same stream and recycled back to the pre-mixer (102);

In an embodiment $AlCl_3$ via stream 1 is mixed with a solvent stream 2 in the pre-mixer (102). The mixing can be either in a batch mode or continuous mode. Initially solvent may be charged followed by slow addition of a metal halide in a continuous or semi-continuous mode. The solvent includes but is not limited to ethyl acetate, ethanol, methanol, methyl iso butyl ketone, methyl ethyl ketone, benzene, toluene, dichloromethane and combinations thereof.

The weight to volume ratio of the metal halide to the solvent may vary from 1:0.5 to 1:10, preferably 1:5. The process can be carried out in the absence of a solvent. Chilled water or chilled brine is circulated inside the jacket in order to remove heat liberated in the pre-mixer. The pre-mixed feed is then transferred to a reactor (104) via stream 3. In the reactor (104) triethylamine is added via stream 4 either in a semi continuous mode or continuous mode. After addition, mixing time of 30 mins to 5 hrs can be given in order to ensure complete ionic salt precursor formation.

In one embodiment the addition sequence can be changed i.e triethylamine via stream 1 is mixed with a solvent stream 2 in the pre-mixer (102). The pre-mixed feed is then transferred to the reactor (104) via stream 3. In the reactor (104), $AlCl_3$ is added via stream 4 either in a semi continuous mode or continuous mode.

After the addition, mixing time of 30 mins to 5 hrs can be given in order to ensure complete ionic salt precursor formation.

The slurry mass is then transferred to the filter (106) via stream 5 where the solids get filtered off. These solids are transferred to the dryer (108) to get complete dried ionic salt precursor.

In one embodiment optionally a solvent wash may be given to the wet solid to avoid drying operation. The solvent includes but is not limited to benzene, toluene, dichloromethane and the like.

The filtrate obtained from (106) is subjected to distillation (110) via stream 14 where amine and solvent are distilled off and recycled back to (104) and (102) respectively. Alternatively the stream 14 can be directly recycled to (102) without distillation (110). The residual solvent obtained from the dryer (108) is directly recycled to (102) via stream 8.

The ionic salt complex precursor is mixed with $AlCl_3$ to form the ionic liquid compound FIG. 2 of the accompanying drawings illustrates a process flow diagram for the preparation of the ionic liquid compound/catalyst. The process is carried out in either a batch or semi-continuous or continuous mode.

In FIG. 2 of the accompanying drawings, (112) represents a second pre-mixer for mixing the dried ionic salt precursor and solvent in step, the pre-mixer (112) can be either a batch or continuous, jacketed stirred vessel or static mixer or jet mixer or pump mixer;

(114) represents a reactor where ionic liquid formation takes place from the precursor and metal halide, the reactor (114) can be a jacketed stirred vessel, static mixer, slurry reactor or combinations thereof.

In one embodiment the ionic salt precursor is transferred to the pre-mixer (112) via stream 9 where it is mixed with a suitable solvent which is transferred via stream 10. The ionic salt precursor utilized may be dried or solvent washed. The solvent includes but is not limited to benzene, toluene, dichloromethane and combinations thereof. The obtained slurry is then transferred to the reactor (114) via stream 11, where $AlCl_3$ is added via stream 12 to the slurry to form ionic liquid. The addition of $AlCl_3$ can be continuous or semi-continuous. After addition, mixing time of 30 mins to 5 hrs can be given in order to ensure complete ionic liquid formation. This ionic liquid compound/catalyst is then collected via stream 13.

In accordance with another aspect of the present disclosure there is provided a process for conducting at least one reaction selected from the group consisting of alkylation reaction, arylation reaction, acylation reaction, diels alder reaction and oligomerization reaction of at least one compound selected from the group consisting of $C_1$ to $C_{20}$ aliphatic compounds, $C_6$ to $C_8$ aromatic compounds and heteroaryl compounds in the presence of an ionic liquid compound represented by formula $[(NR_1R_2R_3)_iM_1]^{n+}$ $[(M_2Y_k)_L X_j]^{n-}$.

In one embodiment the reaction is carried out using at least one reactant selected from the group consisting of olefins, paraffins, alkyl or aryl halides, dialkyl or diaryl sulfates, dialkyl or diaryl carbonates, alcohols, carboxylic acids, esters, thiols and carbenes.

In one embodiment the reactant is olefin or a mixture of olefins having carbon atoms ranging from 2 to 50.

In accordance with the present disclosure the volume ratio of ionic liquid compound to the compound ranges from 0.01 to 1.5. The ionic liquid compound utilized is selected from the group consisting of fresh ionic liquid compound, recycled ionic liquid compound and a combination thereof. The process further includes a step of recovering and recycling of said ionic liquid compound.

In accordance with one exemplary embodiment there is provided a process for alkylation of benzene in the presence of an ionic liquid compound of the present disclosure and at least one alkylating agent to obtain linear alkyl benzene. The alkylation of benzene is carried out at a temperature of 20 to 100° C., preferably at 30 to 60° C. The alkylating agent used is olefin selected from the group consisting of $C_{10}$ to $C_{14}$ olefins and mixtures thereof. Alternatively, the alkylating agent is a mixture of at least one $C_2$ to $C_{50}$ containing olefin and at least one $C_2$ to $C_{50}$ containing paraffin.

The ratio of benzene to the alkylating agent ranges from 1:1 to 20:1, preferably, 6:1 to 10:1.

The alkylation of benzene is carried out at a pressure ranging from 1 to 10 atmospheres, preferably 1 to 6 atmospheres.

The process further includes recovering amine such as trialkylamine or triaryl amine from the used or deactivated ionic liquid.

The alkylation process is illustrated herein below with the help of accompanying drawing (FIG. 3), In FIG. 3 of the accompanying drawings, (116) represents a first mixer;
(118) represents a second mixer; the mixers M1 & M2 can be either a stirred vessel or plug flow reactor or static mixer or jet mixer or pump mixer or combinations thereof;
(120) represents a first settler, the settler can be a gravity settling vessel, either horizontal or vertical, it can be a single step settling or a multi-step settling with a series of settlers, either horizontal or vertical;
(122) represents a third mixer which can be either a stirred vessel or static mixer or jet mixer or pump mixer;
(124) represents a second settler, it can be a gravity settling vessel, either horizontal or vertical, it can be a single step settling or a multi-step settling with a series of settlers, either horizontal or vertical;
optionally, there can be only one mixer (116) with one settler where the said mixer (116) can be either of the stirred vessel, static mixer, jet mixer and pump mixer or two mixers 116 & 118 with two settlers where the said mixers 116 & 118 can be a stirred vessel or static mixer or jet mixer or pump mixer and combinations thereof, or
optionally, another settler can be included between 116 & 118 if required;
(126) represents a purifier which can be a stirred vessel or centrifuge separator or packed column packed with alumina to remove acid traces;
(128) represents a third settler;
(132) represents a first fractionating column;
(134) represents a second fractionating column;
(136) represents a third fractionating column; and
(130) represents a catalyst recovery unit.

In one embodiment, a pre-mixed feed is prepared by mixing benzene and olefin streams coming from lines 1 & 2 respectively. The pre-mixed feed is then fed to the mixer (116) where fresh/recycled/regenerated catalyst is added via line 3. In another embodiment the catalyst (ionic liquid compound) and benzene can be mixed in another pre-mixer and fed to the mixer (116).

In one embodiment the olefin feed stream can be pure olefin, a mixture of olefins and paraffin's with carbon atoms ranging from 2-50, preferably 10-15.

In another embodiment the mixed olefin stream contains 85-90 wt % paraffin's and 10-15 wt % olefins.

The alkylation reaction takes place in the mixer (116). The outlet of 116 is directly fed into second mixer (118) where further reaction takes place. The temperature and pressure conditions in 118 can be same as 116 or can be different. Optionally, there can be a settler between 116 & 118 where the reaction mixture from 116 can be fed to the settler and after the layer separation the upper hydrocarbon layer is transferred to 118 along with a fresh catalyst and the lower catalyst layer can be recycled to the mixer 116/118 directly or through the catalyst recovery unit (130).

In a specific embodiment the olefin stream can be split and send simultaneously to the mixer 116 & 118 which gives an advantage of enhancing the mole ratio of benzene to olefin.

The outlet from 118 is fed into the settler (120) where hydrocarbon and catalyst layers are separated. The heavier catalyst layer from (120) via line 4 is recycled to the mixer 116/122 directly or through the catalyst recovery unit (130). The upper layer is hydrocarbon layer which is fed to the mixer (122) via line 5 where fresh/recycled/regenerated catalyst is added via line 3. The outlet from 122 is fed into the settler (124) where hydrocarbon and catalyst layers are separated. Optionally, there can be only one mixer 116 instead of 116, 118 & 122 where the outlet of 116 is fed into the settler (124) or optionally there can be two mixers 116 & 118 where the outlet of 118 is fed into settler (124). The heavier catalyst layer from 124 via line 6 is recycled to the mixer 116/122 through 130. The upper hydrocarbon layer is fed to hydrocarbon layer purifier (126) via line 7, where the deacidification of hydrocarbon layer takes place.

In a specific embodiment hydrocarbon layer is washed with either water or alkali solution via line 8 or directly centrifuged without any addition of water or alkali solution to remove trace acid content in the hydrocarbon layer.

In one embodiment the volume ratio of water or alkali solution to hydrocarbon layer is in the range of 0.2 to 1 and the concentration of alkali may ranges from 2-50% in alkali solution.

In one embodiment the purifier (126) can also be a packed column filled with alumina base to remove acidic traces in hydrocarbon layer. In another embodiment the purifier can also be a stripper column where the acid traces will be removed by heating the hydrocarbon layer there by partial removal of benzene along with acid. In another embodiment the said purifier can also be a combination of stripper column and packed column filled with alumina base or vice versa.

The outlet of 126 is directly fed to the settler (128) where layer separation occurs. In case of water or alkali wash the bottom layer will be aqueous layer with large quantity, which is sent for effluent treatment via line 9 while in case of centrifugation or crystallization, the bottom layer will be a catalyst layer with very small quantity which is fed into (130) via line 9. The upper hydrocarbon layer from 128 is fed into the fractionating column (132) where benzene is distilled off and recycled to line 1 via line 11. The residue of 132 is fed to the fractionating column 134 via line 12 to remove and recover paraffin via line 13. The residue of the fractionating column (134) is fed to the fractionating column (136) to separate linear alkyl benzene product by line 15 and heavy alkylated product by line 16.

In one embodiment the distillation columns 132, 134 & 136 can be operated under pressure or atmospheric pressure or under vacuum.

The process of the present disclosure is further illustrated herein below with the help of the following examples. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

EXAMPLE-1

Preparation of Triethylamine—Aluminum Chloride Salt Precursor 8.08 gm (0.061 mol) of $AlCl_3$ and 50 ml of ethyl acetate were charged into a 250 ml RB flask under $N_2$ atmosphere.

Slowly under stirring, 18.4 gm (0.0182 mol) of triethylamine was added for 30 minutes at 15-20° C. to obtain a mass. The whole mass was then stirred for 4 hrs. The resultant mixture was then separated by filtration. The solids were washed with 100 ml fresh ethyl acetate followed by drying to get 22 gm of triethylamine-Aluminum chloride salt precursor.

EXAMPLE-2

Preparation of Ionic Liquid 15 gm (0.034 mol) of total solid powder obtained in the EXAMPLE-1 and 20 ml benzene were charged into a 100 ml single neck RB flask kept on a magnetic stirrer. $N_2$ flow was ensured inside the flask. The flask was kept in a water bath at 10-15° C. A magnetic needle was kept inside the flask for stirring. Slowly, 27.5 gm (0.206 mol) of $AlCl_3$ was added to the flask under stirring for 30 minutes. The obtained mass was stirred for 3-4 hrs. The resultant ionic liquid was kept under closed conditions.

EXAMPLE-3

Preparation of Ionic Liquid 15 gm (0.034 mol) of total solid powder obtained in the EXAMPLE-1 was charged into a 100 ml single neck RB flask kept under overhead stirrer. $N_2$ flow was ensured inside the flask. The flask was kept in a water bath at 10-15° C. Slowly, under stirring 29.3 gm (021 mol) of $AlCl_3$ was added to the flask under stirring for 30 minutes. The obtained mass was stirred for 3-4 hrs. The resultant ionic liquid was kept under closed conditions.

EXAMPLE-4

Alkylation Reaction 52.02 liters of hydrocarbon stream containing 10-13% C10-C14 olefins & 87-90% paraffins and 20.02 liters of benzene were charged into a 250 L glass reactor kept under an overhead stirrer, placed in a heating mantle. $N_2$ flow was ensured inside the reactor. The reactor was then heated to 38-39° C. Once the temperature was achieved, 0.7 kg of the ionic liquid catalyst prepared as per EXAMPLE-2 was added to the reactor and stirred for 5 minutes. After 5 minutes the reaction mass was allowed to settle for 10 minutes. The layers were then separated. The upper hydrocarbon layer was then analysed. The conversion of benzene to linear alkyl benzene was found to be 99.7%,

EXAMPLE-5

The lower catalyst layer obtained from EXAMPLE-4 was recycled with fresh hydrocarbon stream and benzene as per the procedure provided in EXAMPLE-3. The conversion of benzene to linear alkyl benzene was found to be 99.7%.

EXAMPLE-6

Alkylation Reaction 141.5 ml (124.3 gm) of benzene was added to a 250 ml RB flask kept under an overhead stirrer under N2 atm. 7.5 gm of ionic liquid catalyst prepared as per EXAMPLE-2 was added to the flask. 23.4 ml benzyl chloride was added to flask at 45-46° C. and stirred for 15 min. After completion of reaction, catalyst and hydrocarbon layers were separated. The upper hydrocarbon layer was then analysed by gas chromatography for benzyl chloride conversion. The conversion of benzyl chloride to biphenyl methane was found 90%.

EXAMPLE-7

The lower catalyst layer obtained from EXAMPLE-6 was recycled with fresh benzene and benzyl chloride as per the procedure provided in EXAMPLE-6. The conversion of benzyl chloride was found 90%.

EXAMPLE-8

Oligomerization 100 mL of hydrocarbon stream containing 10-13% C10-C14 olefins and 87-90% paraffins were charged into a 250 mL glass reactor kept under an overhead stirrer, placed in a heating mantle, $N_2$ flow was ensured inside the reactor. The reactor was then heated to 45° C. Once the temperature was achieved, 0.1 g of the ionic liquid catalyst prepared as per EXAMPLE-2 was added to the reactor and stirred for 10 minutes. After 10 minutes the reaction mass was allowed to settle for 10 minutes. The layers were then separated. The upper hydrocarbon layer was then analysed. The conversion of olefins was found to be 96.15%.

EXAMPLE-9

Alkylation of Phenol 23.5 g of Phenol and 2.2 g Methyl tert-butyl ether (MTBE) were charged into a 100 mL glass reactor kept under an overhead stirrer, placed in a heating mantle. $N_2$ flow was ensured inside the reactor. The reactor was then heated to 60° C. Once the temperature was achieved, 0.25 g of the ionic liquid catalyst prepared as per EXAMPLE-2 was added to the reactor and stirred for 3 hrs, After 3 hrs the reaction was workup with 25 mL distilled water. The conversion of MTBE was found to be 95%.

EXAMPLE-10

Diels Alder Reaction 2.76 g of Isoprene and 1.02 g Vinyl Acetate were charged into a 100 mL glass reactor kept under an overhead stirrer, placed in a heating mantle. $N_2$ flow was ensured inside the reactor. The reactor was then heated to 60° C. Once the temperature was achieved, 0.03 g of the ionic liquid catalyst prepared as per EXAMPLE-2 was added to the reactor and stirred for 4 hrs. After 4 hrs the reaction was workup with 10 mL ethyl acetate. The conversion of reactants was found to be 98%.

EXAMPLE-11

Acylation of Benzene by Acetyl Chloride 19.5 g of Benzene and 3.5 g Acetyl Chloride were charged into a 100 mL glass reactor kept under an overhead stirrer, placed in a heating mantle. $N_2$ flow was ensured inside the reactor. The reactor was then heated to 60° C. Once the temperature was achieved, 0.21 g of the ionic liquid catalyst prepared as per EXAMPLE-2 was added to the reactor and stirred for 2 hrs. After 2 hrs the reaction was workup with 25 mL distilled water. The conversion of Acetyl Chloride was found to be 98%.

EXAMPLE-12

Acylation of Benzene by Benzoyl Chloride 19.5 g of Benzene and 1.95 g Benzoyl Chloride were charged into a 100 mL glass reactor kept under an overhead stirrer, placed in a heating mantle. $N_2$ flow was ensured inside the reactor. The reactor was then heated to 60° C. Once the temperature was achieved, 0.21 g of the ionic liquid catalyst prepared as per EXAMPLE-2 was added to the reactor and stirred for 3 hrs. the reaction was workup with 15 mL distilled water & 15 mL ethyl acetate. The conversion of Benzoyl Chloride was found to be 90%.

EXAMPLE-13

Synthesis of $AlCl_3$-TEA/$ZnCl_2$ Ionic Liquid 10 g of $AlCl_3$-TEA ionic salt precursor was charged into a 100 mL glass reactor kept under an overhead stirrer, placed in a water bath. Then, 18.66 g Zinc Chloride was slowly added in to it with constant stirring. $N_2$ flow was ensured inside the reactor. The mixture was stirred for 3 hrs to get viscous ionic liquid.

EXAMPLE-14

Synthesis of $SbCl_3$-TEA/$FeCl_3$ Ionic Liquid 22.5 g of $SbCl_3$ and 100 mL ethanol were charged into a 250 mL glass reactor kept under an overhead stirrer, placed in a water bath. Then, 36 g TEA was slowly added in to it with constant stirring. $N_2$ flow was ensured inside the reactor. The mixture was stirred for 4 hrs to get white coloured solid. The reaction mass was allowed to settle for 10 minutes. The solid was then separated and dried at 100° C. 10 g of $SbCl_3$-TEA ionic salt precursor was charged into a 100 mL glass reactor kept under an overhead stirrer, placed in a water bath. Then, 18.31 g $FeCl_3$ was slowly added in to it with constant stirring. $N_2$ flow was ensured inside the reactor. The mixture was stirred for 3 hrs to get viscous ionic liquid.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:
1. An ionic liquid compound of Formula (I):

Formula I
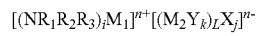

wherein,
$NR_1R_2R_3$ represents an amine,
$R_1$, $R_2$ and $R_3$ are independently selected from the group consisting of alkyl, aryl and H,
$M_1$ or $M_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof,
X or Y is selected from the group consisting of halogen, nitrate, sulphate, sulfonate, carbonate, phosphonate and acetate,
'n' represents 1 to 4,
'i' represents 1 to 6,
'j' represents 1 to 4,
'k' represents 1 to 4,
'L' represents 1 to 7,
$M_1$=$M_2$ or $M_1$≠$M_2$, and
X=Y or X≠Y.

2. The ionic liquid compound as claimed in claim 1, wherein the alkyl group is selected from the group consisting of methyl, ethyl, propyl, butyl and combinations thereof; the aryl group is selected from the group consisting of benzyl, phenyl, substituted benzenes and combinations thereof; and the halogen is selected from the group consisting of F, Cl, Br and I.

3. The ionic liquid compound as claimed in claim 1, wherein $NR_1R_2R_3$ is a trialkylamine; $M_1$ or $M_2$ is a metal selected from the group consisting of Al, Fe, Zn, Mn, Mg, Ti, Sn, Pd, Pt, Rh, Cu, Cr, Co, Ce, Ni, Ga, In, Sb, Zr and combinations thereof; and X or Y is a halogen.

4. A process for the preparation of an ionic liquid compound of Formula (I),

Formula I
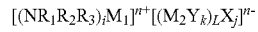

wherein,
$NR_1R_2R_3$ represents an amine,
$R_1$, $R_2$ and $R_3$ are independently selected from the group consisting of alkyl, aryl and H, $M_1$ or $M_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof, X or Y is selected from the group consisting of halogen, nitrate, sulphate, sulfonate, carbonate, phosphonate and acetate, 'n' represents 1 to 4, 'i' represents 1 to 6, 'j' represents 1 to 4, 'k' represents 1 to 4, 'L' represents 1 to 7, $M_1=M_2$ or $M_1 \ne M_2$, and X=Y or X≠Y, said process comprising the following steps:

i. preparing an ionic salt complex precursor represented by Formula $[(NR_1R_2R_3)_iM_1]^{n+}[X_j]^{n-}$ by mixing an amine represented by Formula $NR_1R_2R_3$ and a metal salt represented by formula $M_1X_j$; and ii. mixing the ionic salt complex precursor and a metal salt represented by formula $M_2Y_k$ to obtain the ionic liquid compound.

5. The process as claimed in claim 4, wherein the step (i) and/or the step (ii) are carried out at a temperature ranging from −20 to 100° C.

6. The process as claimed in claim 4, wherein the step (i) is carried out in the presence of a solvent selected from the group consisting of ethyl acetate, ethanol, methanol, methyl iso butyl ketone, methyl ethyl ketone, benzene, toluene, dichloromethane and combinations thereof and the step (ii) is carried out in the presence of a solvent selected from the group consisting of benzene, toluene, dichloromethane, methyl iso butyl ketone, methyl ethyl ketone and combinations thereof.

7. The process as claimed in claim 4, wherein the mole ratio of the amine to the metal salt ranges from 1:0.1 to 1:0.5 and the mole ratio of the ionic salt complex precursor to the metal salt ranges from 1:3 and 1:6.

8. The process as claimed in claim 4, wherein ionic liquid compound is $[(Et_3N)_3-Al]^{3+}[(AlCl_3)_6Cl_3]^{3-}$ prepared by mixing triethylamine and $AlCl_3$ to form ionic salt complex precursor, $[(Et_3N)_3-Al]^{3+}[(Cl)_3]^{3-}$, and complexing said ionic salt complex precursor with $AlCl_3$.

9. An ionic salt complex precursor represented by Formula (II)

$$[(NR_1R_2R_3)_iM_1]^{n+}[X_j]^{n-} \quad \text{Formula II}$$

wherein, $NR_1R_2R_3$ represents an amine, $R_1$, $R_2$ and $R_3$ are independently selected from the group consisting of alkyl, aryl and H, $M_1$ or $M_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof, X or Y is selected from the group consisting of halogen, nitrate, sulphate, sulfonate, carbonate, phosphonate and acetate, 'n' represents 1 to 4, 'i' represents 1 to 6, and 'j' represents 1 to 4.

10. A process for preparing an ionic salt complex precursor as claimed in claim 9 comprises mixing an amine represented by Formula $NR_1R_2R_3$ and a metal salt represented by formula $M_1X_j$.

11. The process as claimed in claim 10, wherein said ionic salt complex precursor is $[(Et_3N)_3-Al]^{3+}[(Cl)_3]^{3-}$ prepared by mixing triethylamine and $AlCl_3$.

12. A process for conducting at least one reaction selected from the group consisting of alkylation reaction, arylation reaction, acylation reaction, diels alder reaction and oligomerization reaction of at least one compound selected from the group consisting of $C_1$ to $C_{20}$ aliphatic compounds, $C_6$ to $C_8$ aromatic compounds and heteroaryl compounds in the presence of an ionic liquid compound represented by formula $[(NR_1R_2R_3)_iM_1]^{n+}[(M_2Y_k)_L\,X_j]^{n-}$ and at a temperature of 20 to 100° C., wherein, $NR_1R_2R_3$ represents an amine, $R_1$, $R_2$ and $R_3$ are independently selected from the group consisting of alkyl, aryl and H, $M_1$ or $M_2$ is a metal selected from the group consisting of Al, Fe, Zn, Mn and Mg, Ti, Sn, Pd, Pt, Rh, Cu, Cr, Co, Ce, Ni, Ga, In, Sb, Zr and combinations thereof, X or Y is selected from the group consisting of halogen, nitrate, sulphate, sulfonate, carbonate, phosphonate and acetate, 'n' represents 1 to 4, 'i' represents 1 to 6, 'j' represents 1 to 4, 'k' represents 1 to 4, 'L' represents 1 to 7, $M_1=M_2$ or $M_1 \cdot M_2$, and X=Y or X≠Y.

13. The process as claimed in claim 11, wherein said reaction is carried out using at least one reactant selected from the group consisting of olefins, paraffins, alkyl or aryl halides, dialkyl or diaryl sulfates, dialkyl or diaryl carbonates, alcohols, carboxylic acids, esters, thiols and carbenes.

14. The process as claimed in claim 12, wherein the reactant is olefin or a mixture of olefins having carbon atoms ranging from 2 to 50.

15. The process as claimed in claim 11, wherein the volume ratio of ionic liquid compound to the compound ranges from 0.01 to 1.5.

16. The process as claimed in claim 11, includes a step of recovering and recycling of said ionic liquid compound.

17. The process as claimed in claim 11, wherein said ionic liquid compound is selected from the group consisting of fresh ionic liquid compound, recycled ionic liquid compound and a combination thereof.

18. The process as claimed in claim 11, wherein said reaction is an alkylation of benzene; said reaction comprises alkylating benzene at a temperature of 20 to 100° C., preferably at 30 to 60° C. and at a pressure ranging from 1 to 10 atmospheres, preferably 1 to 6 atmospheres, in the presence of an ionic liquid compound represented by formula $[(NR_1R_2R_3)_iM_1]^{n+}[(M_2Y_k)_L\,X_j]^{n-}$ and at least one alkylating agent to obtain linear alkyl benzene.

19. The process as claimed in claim 17, wherein the alkylating agent is a mixture of at least one $C_2$ to $C_{50}$, preferably $C_{10}$ to $C_{14}$, olefin and at least one $C_2$ to $C_{50}$ containing paraffin.

20. The process as claimed in claim 17, wherein the ratio of benzene to the alkylating agent ranges from 1:1 to 20:1, preferably, 6:1 to 10:1.

* * * * *